United States Patent [19]

Maüz et al.

[11] Patent Number: 4,542,069

[45] Date of Patent: Sep. 17, 1985

[54] VINYLENE CARBONATE POLYMERS, A PROCESS FOR THEIR PREPARATION AND THEIR USE

[75] Inventors: Otto Maüz, Liederbach; Klaus Sauber, Bad Soden am Taunus; Siegfried Noetzel, Kelkheim, all of Fed. Rep. of Germany

[73] Assignee: Hoechst Aktiengesellschaft, Fed. Rep. of Germany

[21] Appl. No.: 554,637

[22] Filed: Nov. 23, 1983

[30] Foreign Application Priority Data

Nov. 25, 1982 [DE] Fed. Rep. of Germany ....... 3243591

[51] Int. Cl.$^4$ .................. C08F 218/24; B32B 5/16
[52] U.S. Cl. .................. 428/402; 526/201; 526/314
[58] Field of Search ............... 526/314, 201; 428/402

[56] References Cited

U.S. PATENT DOCUMENTS

| | | | |
|---|---|---|---|
| 2,932,629 | 4/1960 | Wiley | 526/201 |
| 3,553,183 | 1/1971 | Field | 260/78.5 |
| 4,070,348 | 1/1978 | Kraemer et al. | 526/261 |
| 4,098,771 | 7/1978 | Huemer et al. | 526/209 |

FOREIGN PATENT DOCUMENTS

| | | | |
|---|---|---|---|
| 2014242 | 10/1970 | Fed. Rep. of Germany . | |
| 2237316 | 2/1974 | Fed. Rep. of Germany . | |
| 2407340 | 9/1974 | Fed. Rep. of Germany . | |
| 2556759 | 6/1977 | Fed. Rep. of Germany . | |
| 51-36237 | 3/1976 | Japan | 526/201 |
| 56-92901 | 7/1981 | Japan | 526/314 |
| 899205 | 6/1962 | United Kingdom | 526/314 |
| 1009004 | 8/1962 | United Kingdom . | |
| 1571182 | 7/1980 | United Kingdom . | |

*Primary Examiner*—Joseph L. Schofer
*Assistant Examiner*—Peter F. Kulkosky
*Attorney, Agent, or Firm*—Finnegan, Henderson, Farabow, Garrett & Dunner

[57] ABSTRACT

The invention relates to bead polymers based on vinylene carbonate which are distinguished, in particular, by high porosity and which are well suited as carrier materials for biologically active substances.

The preparation of these bead polymers is carried out, according to the invention, in the presence of certain dispersion stabilizers.

12 Claims, No Drawings

VINYLENE CARBONATE POLYMERS, A PROCESS FOR THEIR PREPARATION AND THEIR USE

The binding, via covalent bonds, of biologically active substances, such as enzymes, antibodies, antigens, hormones and the like, with retention of their activity, to polymeric carrier materials, in order by this means, for example, to stabilize or purify enzymes or make them insoluble in water, is known. Biologically active substances immobilized in this manner offer considerable advantages compared with the soluble form: on the one hand, the removability, by sedimentation, after completion of a reaction is simplified and, on the other hand, the stability and reusability of the products are multiplied, since any proteases which may be present are also bound.

Swellable, crosslinked bead polymers, which are obtained by copolymerization of monomers containing reactive groups, crosslinked monomers and hydrophilic monomers, are described as carrier substances in German Auslegeschrift No. 2,237,316. The reactive groups disclosed in this are the halogenoalkyl, the epoxide, the carbonyl chloride, carboxylic anhydride, carbonyl azide, carboxylic phenyl ester and hydroxamic acid groups. However, these carrier materials have a number of disadvantages; thus, binding the biologically active substances to some of them is rather elaborate and frequently takes several days; moreover, when using the anhydride variants, charges are introduced.

According to German Offenlegungsschrift No. 2,407,340, polymers and copolymers of vinylene carbonate are used for bonding biologically active substances. According to German Auslegeschrift No. 2.552.510 also, copolymers of vinylene carbonate can be employed for this purpose. According to a variant of the process described therein, the cyclocarbonate groups still present after binding the biologically active substances are converted into hydroxyl groups.

The polymeric carriers which are based on vinylene carbonate as the reactive monomer unit and which are disclosed in these two printed publications do have the advantage, compared with other carrier materials, of a lower non-specific adsorption of biologically active substances, for example when used as affinity adsorbents; moreover, they can be readily modified. However, they lack the morphology of the bead form and the requisite porosity. Thus, for example, they cannot be used for column processes.

Vinylene carbonate copolymers of irregular form are produced by the procedure described in German Offenlegungsschrift No. 2,556,759, according to which the polymerization is carried out in a non-polar organic dispersant in the presence of certain non-ionic dispersion stabilizers. Again, these polymers are not in the form of beads nor do they have the necessary porosity.

Thus, the object of the present invention was to provide a polymeric material, in particular a carrier material for biologically active substances, based on vinylene carbonate, which does not have the disadvantages of the state of the art and which, in particular, is in the form of beads and has adequate porosity. Another object was to develop a process suitable for this purpose.

Hence, to achieve this object, the invention proposes a polymer which is essentially composed of units which are derived from vinylene carbonate or a derivative thereof which is substituted by a monovalent hydrocarbon radical having up to 8 carbon atoms, and of at least one other monomer which can be copolymerized with it, the mean particle size of the polymer particles being in the range from 20 to 800 μm, which comprises the polymer particles having an essentially spherical shape and a mean pore diameter of 5 to 1,000 nm.

The preparation of a bead polymer of this type is carried out, according to the invention, by a process in which vinylene carbonate or a derivative which is substituted by a monovalent hydrocarbon radical having up to 8 carbon atoms is polymerized, in a liquid dispersing medium which, under the polymerization conditions, does not dissolve the monomers, the polymer and, preferably, the initiator, in the presence of a radical initiator and a dispersion stabilizer, with at least one monomer which can be copolymerized with vinylene carbonate, which comprises using, as the dispersion stabilizer, a copolymer of maleic anhydride and a vinyl alkyl ether having 6 to 30 carbon atoms in the alkyl group or a vinyl ester having 6 to 30 carbon atoms in the carboxylic acid group or a relatively long-chain α-olefin having 8 to 30 carbon atoms.

The invention also relates to the use of the polymers thus obtained as carrier materials for the preparation of carrier-bound biologically active substances.

The bead polymer according to the invention advantageously contains the units which are derived from vinylene carbonate or its derivatives in amounts of 5 to 90 mole-%, preferably 10 to 80 mole-%, relative to the total polymer. In principle, amounts which are larger or smaller than those indicated above are possible but, as a rule, this is associated with disadvantages. The optimal amount per se of the units derived from vinylene carbonate or from its derivatives within the ranges indicated above, depends, inter alia, on the desired site density, on the molecular weight of the biologically active substance and the like.

According to the invention, vinylene carbonate is preferred as the monomer which provides the bead polymer with reactive groups. The derivatives thereof which can likewise be employed according to the invention are those of the formula

in which R represents a monovalent hydrocarbon radical having up to 8 carbon atoms, preferably an alkyl radical having 1 to 6 carbon atoms, and in particular one having to 4 carbon atoms. Examples of these are: the methyl, ethyl, isopropyl, 2-ethylhexyl, n-heptyl, cyclopentyl, allyl, phenyl, tolyl, benzyl or xylyl radical.

If, before being used as a carrier material, the bead polymer according to the invention is modified with so-called spacers (in this context, see below), then, in addition to unchanged vinylene carbonate units according to (I) or 1,2-vinylenediol units (in the case of foregoing hydrolysis), it also contains units appropriately modified with the spacer. These will usually correspond to the formula (II) below, i.e. as a rule, only one spacer unit will be present on neighboring carbon atoms in the polymer chain:

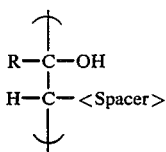 (II)

In this connection, R has the above meaning and <spacer> particularly represents

A—B—C in which A equals 0 or OCONH, B represents an organic radical (the spacer in the narrower sense), in particular a hydrocarbon radical having 1 to 12 carbon atoms, which can optionally be interrupted by heteroatoms, such as 0, NH, S etc., and C represents a functional group which can undergo covalent bonding with the biologically active compound. These include, for example, the groups COOH, NH$_2$,

COX (X=H, halogen, N$_3$, OR; R=alkyl radical having 1 to 6 carbon atoms), CH(OR)$_2$ (R as previous),

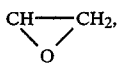 (R as previous),

N$_2$ or NCO.

Preferably, A equals 0, B denotes an aliphatic, in particular an unbranched, hydrocarbon radical having 1 to 6 carbon atoms, an aryl radical or an alkylaryl radical and C equals NH$_2$, or

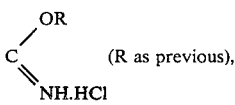

Examples of the group A—B—C are:

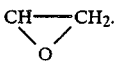

| | |
|---|---|
| —O—(CH$_2$)$_n$—NH$_2$; | n = 2-12 |
| 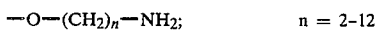 | n = 1-8 |
| 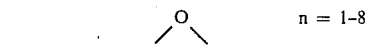 | n = 1-8 |
| 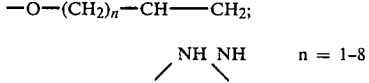 | n = 1-8<br>X = H, OH, halogen, N$_3$, or |
| 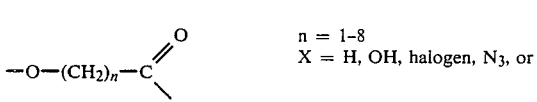 | n = 1-6<br>R = alkyl radical having 1-6 carbon atoms |
| 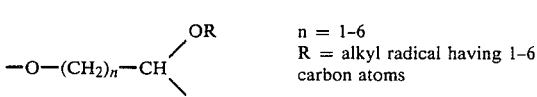 | n = 2-8<br>R = alkyl radical having 1-6 carbon atoms |
| 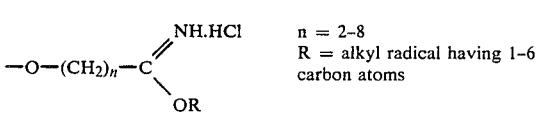 | Y = NH$_2$, N$_2$, NCO |

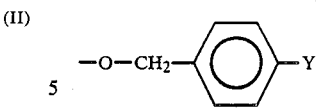

The indicated amount in mole-% of monomer units according to (II) or of spacers, relative to all the units derived from vinylene carbonate, is up to Y$_1$ mole-%, in particular Y$_2$ mole-%, where Y$_1$ = 91 − 0.00753 X$^2$ and

Y$_2$ = 95 − 0.94 X and X is the number of mole-% of all the units derived from vinylene carbonate related to the total monomers. The minimum amount, indicated in mole-%, of monomer units according to (II) or of spacers is 0.01 mole-%, preferably 0.5 mole-%, relative to the total monomers. In general, the maximum amount of these monomer units will not exceed about 35 mole-%, relative to the total monomers.

According to the invention, the bead polymer also contains at least one other monomer unit which derives from a monomer which can be copolymerized with vinylene carbonate. Preferably, this takes the form of two other monomer units which differ from one another.

One of these is preferably a monomer having hydrophilic groups which provide the polymer employed as carrier with adequate hydrophilicity and thus swellability. This is of importance inasmuch as the bonding reaction with the biologically active substance is usually carried out in an aqueous system, and the hydrophilic biologically active substance must be able to diffuse up to the carrier material. These monomers include, for example, the monomers listed as component (c) in German Offenlegungsschrift No. 2,237,316. Those which are preferred within the scope of the present invention are: N-vinylpyrrolidone, (meth)acrylic acid, (meth)acrylamide, (meth)acrylic esters, each having 2 to 4 carbon atoms in the alkyl group, hydroxyalkyl esters of (meth)acrylic acid having 2 to 6 carbon atoms in the alkyl group, N-vinyl-N-alkylacetamide (C$_1$-C$_4$-alkyl) and vinyl acetate. Where appropriate, it is also possible for several of these hydrophilic monomer units to be present.

The ratio of vinylene carbonate to hydrophilic component in the polymer also depends on the type of enzyme to be bonded. When the molecular weight of the enzyme, or of the substrate with which the enzyme is intended to react, is very high, it is advantageous to increase the molar ratio in favor of the hydrophilic component, since neighboring carbonate groups which are capable of bonding do not succeed in reacting, for stearic reasons, and may possibly even interfere. Furthermore, the amount of hydrophilic component is also governed by the amount of the crosslinking component which is preferably present according to the invention. As a rule, the greater the amount of the latter, the greater also the amount of hydrophilic component which will be necessary to provide the carrier polymer with sufficient hydrophilicity and swellability. In general, the amount of hydrophilic monomer unit(s) in the polymer according to the invention is 5 to 70 mole-%, preferably 20 to 50 mole-%, relative to the polymer.

The polymer according to the invention preferably contains, as another compound which can be copolymerized with vinylene carbonate, crosslinking monomer units as are known from the state of the art and are described, for example, in German Offenlegungsschrift No. 2,237,316 as component (b). Typical representatives which may be mentioned here are: divinyl ethers of glycols, such as ethylene glycol divinyl ether, butanediol divinyl ether, hexanediol divinyl ether, N,N'-methylenebisacrylamide, N,N'-methylenebismethacrylamide, ethylene glycol bismethacrylate, butanediol bismethacrylate, triallyl cyanurate, trisacryloylperhydrotriazine, divinylbenzene, divinyl adipate, N,N'-divinylethyleneurea, vinyl acrylate, allyl methacrylate, inter alia. It is also possible for several different crosslinking monomer units to be present. Some of these crosslinkers, for example N,N'-divinylethyleneurea or N,N'-methylenebisacrylamide can also contribute to the hydrophilicity of the polymer.

The amount of the crosslinking monomer unit, and thus the density of crosslinking, in the polymer depends on its use. A low density of crosslinking can be advantageous for enzyme reactions in stirred vessels or for diagnostic aids; on the other hand, if used for column packing, high stability of shape of the bead polymer, and thus high density of crosslinking, is a prerequisite. Thus, depending on the type of use, the amount of cross-linking monomer unit can be up to 60 mole-% relative to the polymer. It is preferably between 5 and 40 mole-%. As already stated above in this context, the amount of crosslinking component has a certain relationship with that of the hydrophilic component. The amount of cross-linking monomer will usually be selected such that the bead polymer swells in tetrahydrofuran by up to 14 times, preferably 0 to 8 times, its original bulk volume.

Non-crosslinked carriers are of interest when the reaction of the carrier with the biologically active substance is to be carried out in a solution of the carrier.

Where appropriate, a non-crosslinked carrier polymer can also be crosslinked in a known manner by subsequent chemical reaction, for example with diamines. In this case, the polymer should contain a somewhat higher proportion of vinylene carbonate groups.

Other non-hydrophilic and non-crosslinking monomer units which can optionally be present are, for example, those which are derived from: acrylic and methacrylic esters having 5–12 carbon atoms in the alkyl radical, (meth)acrylonitrile, vinyl esters having 4–18 carbon atoms in the carboxylic acid, such as vinyl butyrate, vinyl stearate and vinyl esters of branched carboxylic acids having 10–12 carbon atoms; also vinylaromatics, such as styrene or α-methylstyrene. These monomer units can be present in the polymer in amounts of 4 to 40 mole-%, preferably 8 to 20 mole-%, relative to the polymer.

The bead polymer according to the invention is predominantly composed of spherical particles, the mean particle size of which in the dry, non-swollen state is 20 to 800 μm, preferably 50 to 300 μm, the particle size distribution preferably being narrow. The particular optimum particle size of the polymer depends, in particular, on the specific area of use. For example, in a column process carried out under normal pressure, it will be possible to select the particle size, within the limits mentioned above, to be correspondingly larger than for a process under pressure. The beads of the bead polymer according to the invention are principally formed as hollow beads, and this gives rise to high porosity. This is evident by the mean pore diameter which results according to the invention being in the range from 5 to 1,000 nm, preferably 10 to 500 nm, and in particular 20 to 200 nm.

The determination of the pore diameter (pore volume) is carried out in such a manner that first the pore volume is determined by the capillary pressure method (mercury porosimetry) (cf. in this context "Ullmanns Encyklopädie der technischen Chemie" (Ullmanns Encyclopedia of Industrial Chemistry) volume 5, (1980), pages 751–752). The mean pore diameter then results from this by calculation using the equation given in this literature citation on page 752, top of the left-hand column.

The bead polymers according to the invention are particularly suitable as carriers for biologically active substances. However, they can also be employed for other purposes, for example as ion exchangers, adsorbents for chromatographic processes and the like.

The process according to the invention for preparing these bead polymers is carried out under the customary and known conditions for bead polymerization, as are described, for example, in German Offenlegungsschrift No. 2,237,316 or German Offenlegungsschrift No. 2,556,759, but with the innovation that special dispersion stabilizers are used.

These are preferably alternating copolymers of maleic anhydride and a vinyl alkyl ether, preferably a vinyl n-alkyl ether having 6 to 30 carbon atoms, preferably 10 to 20 carbon atoms, in the alkyl group, or a vinyl ester having 6 to 30 carbon atoms, preferably 10 to 20 carbon atoms, in the carboxylic acid group, or a relatively long-chain α-olefin having 8 to 30 carbon atbms, preferably 10 to 20 carbon atoms. Examples of these types of vinyl alkyl ethers, vinyl esters and relatively longchain α-olefins which may be mentioned here are: vinyl octyl ether, vinyl decyl ether, vinyl dodecyl ether, vinyl stearyl ether, vinyl myricyl ether, vinyl ethylhexanoate, vinyl isononanoate, vinyl versatate, vinyl laurate, vinyl stearate, and vinyl esters of branched carboxylic acids having 10 to 12 carbon atoms; 1-octene, 1-decene, 1-dodecene, 1-tetradecene, 1-octadecene and 1-tricosene.

These dispersion stabilizers are effective in amounts as little as 0.001% by weight relative to the total amount of monomers. Usually, amounts of 0.005 to 10% by weight, preferably 0.01–5% by weight, (relative to the total amount of monomers) are used.

The reduced specific viscosity (RSV) of these copolymers which are employed as dispersion stabilizers is, as a rule, between 0.01 and 1.0 [dl/g] (determined in 0.6% strength solution in toluene at 25° C.). The corresponding range which is preferred for the copolymers of maleic anhydride and vinyl alkyl ethers or vinyl esters is 0.05 to 1.0 [dl/g], and for the copolymers of maleic anhydride and relatively long-chain α-olefin is 0.01 to 0.1 [dl/g]. The molar ratio between maleic anhydride and the vinyl alkyl ether or vinyl ester or relatively long-chain α-olefin is preferably 1:1.

Those radical initiators which are suitable according to the invention are those which are readily soluble in the monomer phase and have as low a solubility as possible in the liquid dispersing medium. Examples of these are organic peroxides, such as di-tert.-butyl peroxide, dibenzoyl peroxide, cumene hydroperoxide and cyclohexanone peroxide, or aliphatic azo compounds, such as α,α'-azodiisobutyronitrile, azobiscyanovaleric acid, 1,1'-azocyclohexane-1,1'-dicarbodinitrile and azodicarbonamide. Appropriate redox systems may also optionally be used. The amount of initiator is usually 0.01–5, preferably 0.1–2, % by weight (relative to the total amount of monomers).

The liquid dispersing media used for carrying out the bead polymerization according to the invention are, in particular, those organic compounds which are liquid under normal conditions, have a boiling point above 60° C., preferably in the range 85°–300° C., and which either do not dissolve or, in any event, only dissolve traces of the monomers, the polymer and, preferably, also the initiator under the polymerization conditions, in order to suppress undesired precipitation polymerization. Hydrocarbons having 6–20, preferably 12–16, carbon atoms, in particular paraffins, for example, are well suited. It is also possible to use a mixture of various compounds as the dispersing agents. Examples of suitable hydrocarbons or mixtures of hydrocarbons are n-hexane, n-heptane, n-octane, cyclohexane, isooctane, petroleum fractions with boiling ranges between 90° and 170° C., and low viscosity liquid paraffin (Deutsches Arzneibuch (German Pharmacopeia), 7th edition, DAB 7). The ratio of the monomer phase to the dispersing agent phase can vary within wide limits, for example between 0.5:1 to 1:50, preferably 1:1 to 1:15 (ratio by weight).

In order to achieve as high a porosity of the bead polymer as is possible, preferably certain inert, liquid components are added to the polymerization system or, preferably, to the monomers. These components are to be understood to be those materials in which the monomers are readily soluble or which are readily soluble in the monomers or which are miscible with them, but, on the other hand, are virtually insoluble in the dispersing medium and thus are not miscible with it. According to their behavior toward the appropriate copolymers, the inert components can be divided into swelling and/or precipitating agents. In the case of a hydrophilic matrix, polar inert agents will, as a rule, favor swelling, such as, for example, dimethylformamide, dimethyl sulfoxide, dioxane, water to a certain extent etc., while non-polar substances, such as glycerol triacetate etc., prove to be precipitating agents for the copolymer. The same applies to the converse case, i.e. non-polar solvents will serve as swelling agents for hydrophobic polymers. The optimal inert agent or mixture of inert agents can readily be determined by a few simple routine experiments. In particular, when bead polymers having relatively low degrees of crosslinking are aimed at, it may well be advisable to use a mixture of a polar and a non-polar inert agent. The inert components do not participate in the polymerization, but are coated by the polymer and are dissolved out again during work-up. This produces permanent pores. The pore size can be affected by the type and amount of the inert component, but also depends on the amount of crosslinking component.

The inert components can be used alone or in mixtures. Examples which may be mentioned are: methanol and its higher homologs, ethylene glycol, methylglycol, propylglycol, diethylene glycol, 1,4-butanediol, glycerol, polyethylene glycol, diethylene glycol dimethyl ether, glycerol triacetate, ethylene carbonate, formamide, dimethylformamide, dimethyl sulfoxide, dioxane, water to a certain extent etc.

The amount of inert component added can be widely varied. It depends, inter alia, on the monomer composition of the carrier, in particular its content of crosslinker, the desired porosity (pore size) and of the exact intended use of the carrier polymer. Thus, when the degree of crosslinking is high, a correspondingly large amount of inert component is advisable in order to achieve a specified porosity (pore size). Equally, at one and the same degree of crosslinking, the porosity (pore size) will be larger the more inert component is employed. Obviously, this can only be increased within certain limits, since otherwise the thickness of the walls of the hollow beads, and thus their mechanical stability, becomes too low. In most cases, an amount of inert agent which corresponds to 0.02 to 5 times, preferably 0.04 to 3 times, the amount of monomers employed will provide satisfactory results.

The vinylene carbonate and the other comonomer(s) are employed in amounts such that the resulting polymer has the previously mentioned amounts of monomer units. With this aim, the vinylene carbonate is used, as a rule, in amounts of 5 to 95 mole-%, preferably 10 to 85 mole-%, relative to the total mixture of monomers. On the other hand, the amount of hydrophilic monomers is usually 3 to 60 mole-%, preferably 15 to 35 mole-%, relative to the total mixture of monomers, and the amount of crosslinking monomers, when employed, is up to 60 mole-%, preferably 2 to 35 mole-%, relative to the total amount of monomers.

The process according to the invention is advantageously carried out in a reaction vessel which is provided with a stirring device, at temperatures of, usually, 20°–150° C., preferably 65°–125° C. The particle size of the bead polymer is adjusted in a known manner by the speed of stirring and the phase ratio. It is particularly advantageous to use a vertical cylindrical vessel with a flat base, which is provided with a stirrer which is rotated coaxially and the shaft of which almost reaches the base of the vessel. The reaction vessel is preferably vacuum-tight and can be provided with a reflux condenser, addition funnel, gas introduction tube and temperature measuring device. The heating and cooling of the vessel is generally brought about by a liquid bath, for example an oil bath or water bath.

It is advantageous to carry out the process according to the invention with the exclusion of atmospheric oxygen. Thus, the reaction vessel is flushed before starting with an inert gas, preferably nitrogen.

After completion of the polymerization reaction, the unreacted monomers are removed from the reaction vessel, for example by evaporation under reduced pressure, preferably under a pressure of 0.1–15 Torr. After removing the residual monomers, the dispersing agent is separated from the solid polymer, for example by decantation, filtration or aspiration of the supernatant. The polymer is then, where necessary, washed with a low-boiling organic solvent, for example a hydrocarbon, a lower alcohol or acetone, and finally dried. The polymer is usually dried at a temperature of 20°–100° C., preferably 40°–80° C., while drying under reduced pressure is advisable.

The biologically active substance which is to be bonded to the bead polymers according to the invention takes the form of the known, natural or synthetically prepared materials which are active in vivo or in vitro, such as enzymes, activators, inhibitors, antigens, antibodies, vitamins, hormones, effectors, antibiotics, proteins and the like. The latter term also includes proteins having certain non-protein substituents, such as metal ions, polysaccharides, porphyrin groups, adenine dinucleotide, ribonucleic acid, phospholipids etc. Polypeptide fragments, for example the active parts of enzyme molecules, are also included in the term biologically active substances.

Of the biologically active substances mentioned above, the enzymes are preferred according to the invention.

Examples of enzymes are adenyl deaminase, alcoho dehydrogenase, asparaginase, carboxypeptidase, chymotryp n, diphosphoesterase, α-glucosidase, glucose isomerase, glucose oxidase, glucose-6-phosphate-dehydrogenase, hexo kinase, invertase, β-lactamase, lactase, lactate dehydro genase, various lectins, NAD kinase, neuraminidase, papain, peroxidase, phosphatases (alkaline and acid), 5'-phosphodiesterase, pyruvate kinase, ribonuclease and trypsin.

Examples of other biologically active substances are hormones, such as insulin and the wide variety of pituitary hormones, proteins of the gamma-globulin fraction, for example antibodies of classes G, M, A, D and E, other blood factors, for example antihemophilic factor, the coagulation factors, specific antibodies, for example hepatitis, poliomyelitis, measles, mumps, influenza or rabbit antibodies, antigens, such as hepatitis, polibmyelitis, measles, mumps, influenza or rabbit antigens for purification or stimulating suitable antibody reactions, the antigen (after being made insoluble) remaining in the insoluble form and consequently being unable to penetrate into the body and harm it, as well as general body proteins, such as hemoglobin or albumin.

The reaction bonding the biologically active substance is carried out in a known manner, such as is described, for example, in German Offenlegungsschrift No. 2,407,340 or in German Pat. Nos. 2,215,687, 2,421,789 and 2,552,510. The reaction is usually carried out at room temperature or at temperatures below this. The latter applies, in particular, when the biologically active substance to be bonded is inherently unstable; in this case, the temperatures are then below +10° C., preferably at 0° to +5° C.

The bonding reaction is preferably carried out at a pH in the neighborhood of neutrality, for example at pH 5-9, since most biologically active substances are most stable in this range. Nor is it necessary, as a rule, to maintain strongly acid or alkaline conditions, since the macroporous bead polymers according to the invention react rapidly even in the neutral range with most of the substances in question. The bond which is produced thereby provides sufficient stability for long storage and high stability on use.

The polymer containing vinylene carbonate groups or the hydrolysis product can be used as the carrier for this purpose. However, it will be advantageous in many cases to employ the polymer which has been modified with so-called "spacers". "Spacers" are understood to include compounds which react both with the carrier polymer and with the biologically active substance, and which form, as it were, a bridge between the two. The reaction of the bead polymer according to the invention with the spacer can be carried out either directly or, preferably, after previous hydrolysis of the carbonate groups. The extent of reaction depends inter alia on the bulk of the spacer and the accessibility of the carbonate group or the secondary hydroxyl groups which have been produced from it. Suitable spacers according to the invention are the homo- and hetero-bifunctional compounds known for this, the second functional group of which undertakes the coupling with the biologically active substance to be attached (cf. German Pat. Nos. 2,421,789 and 2,552,510, and Ullmanns Encyclopädie der technischen Chemie, 4th edition, volume 10, page 540 and "Characterization of Immobilized Biocatalysts", Verlag Chemie, Weinheim, 1979, page 53).

The spacers which are preferred according to the invention are those which produce the groups shown below:

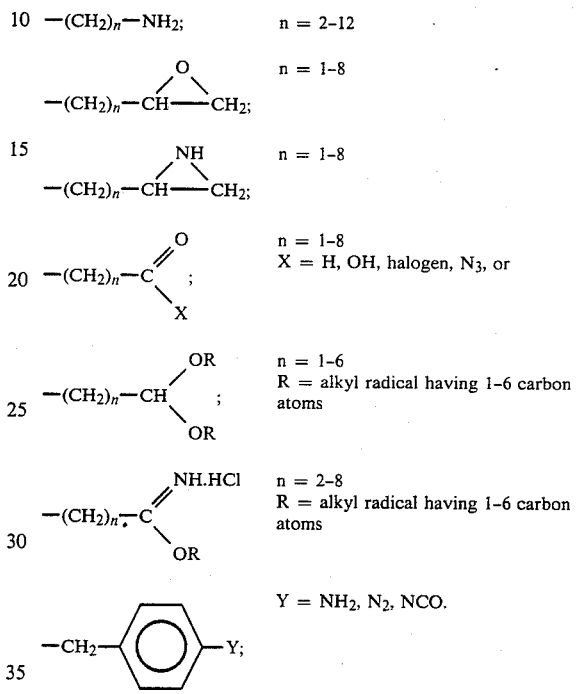

According to an embodiment which is thus preferred according to the invention, the bead polymer is reacted, after hydrolysis of the carbonate groups, with epichlorohydrin, for example.

Preferably about 10 to 80 parts by weight of the carrier polymer, in particular one which contains at least 50 mole-% of vinylene carbonate units, are used per 1 part by weight of the biologically active substance to be bonded. Larger amounts of the carrier polymer can advantageously be employed in the cases in which less than 50 mole-% of the polymer is composed of vinylene carbonate units.

The invention is illustrated in detail by the examples which follow.

Preparation of a dispersion stabilizer (copolymer of maleic anhydride and vinyl stearyl ether) maleic anhydride and vinyl stearyl ether)

98 g of maleic anhydride (1 mole) and 296 g of Vinyl stearyl ether (1 mole) in 250 ml of acetone were initially introduced into a stirred flask, 5 ml of diisopropyl percarbonate (40% strength solution in phthalate) were added, and the mixture was polymerized, with stirring under nitrogen, at 60° for 5 hours. After cooling, the precipitated product was filtered off with suction and washed several times with acetone.

The molar ratio of the two monomers in the copolymer was 1:1; the RSV value was 0.224 [dl/g] (measured in 0.6% strength solution in toluene at 25° C.).

I. Preparation of vinylene carbonate polymers in the form of beads

EXAMPLE 1

(Copolymer of vinylene carbonate, N-vinylpyrrolidone and 1,4-butanediol divinyl ether)

900 ml of low viscosity liquid paraffin DAB 7 (dispersing medium), 0.8 g of a copolymer of maleic anhydride and 1-octadecene (molar ratio 1:1; RSV value 0.064 [dl/g] (measured in 0.6% strength solution in toluene at 25° C.), 4 ml of polyethylene glycol (molecular weight about 400), 43 g of vinylene carbonate, 55.5 g of N-Vinylpyrrolidone, 5 g of 1,4-butanediol divinyl ether and 2 g of azodiisobutyronitrile were initially introduced into a round-bottomed flask with a stirrer, thermometer, nitrogen introduction tube and reflux condenser. The Vinylene carbonate used in this and the following examples was distilled before use over a 1 m long column, which had a silvered jacket and was filled with Raschig glass rings, at 75°/33 Torr. The distilled vinylene carbonate was stored in dark glass bottles under nitrogen in a cold room at about 10°.

The initially introduced mixture was then slowly heated, with stirring. The exothermic polymerization reaction started at about 65°, whereupon the temperature rose to about 80°. This temperature was maintained by means of an oilbath with a thermostat for 2 hours, then the bath temperature was increased to 90° for one hour to complete polymerization. The heating bath was subsequently removed and the batch was allowed to cool to 40°, with stirring. The stirring was then switched off, whereupon the polymer in the form of beads settled out after some time. The major amount of the liquid paraffin was then siphoned off and the residue was subsequently sucked off via a suction filter. The resulting polymer was then treated with petroleum ether, with stirring, in order to remove the adherent liquid paraffin. It was subsequently thoroughly stirred with methanol, and then with acetone, in order to dissolve out the unreacted monomers and the dispersant. Finally, the polymer was dried in a vacuum oven at 50°–60° overnight.

The yield of crosslinked copolymer was 82.8 g (=80% of theory).

Essentially the same product is obtained when a corresponding dispersing agent made from maleic anhydride and dodecene is employed.

EXAMPLE 2

Copolymer of vinylene carbonate, N-vinylpyrrolidone and 1,4-butanediol divinyl ether 900 g of liquid paraffin (DAB 7), 0.2 g of the copolymer of maleic anhydride and vinyl stearyl ether described under a), 4 ml of polyethylene glycol 400, 43 g of vinylene carbonate, 55.5 g of N-vinylpyrrolidone, 20 g of 1,4-butanediol divinyl ether and 2 g of azodiisobutyronitrile were initially introduced into a cylindrical vessel haVing a cross-blade agitator, reflux condenser, thermometer and nitrogen introduction tube. The temperature of the bath was slowly raised to 65°, while passing in nitrogen, then polymerization and working up were carried out as described in Example 1.

The yield of crosslinked product was 92.4 g (=78% of theory).

An essentially identical product is obtained when a corresponding copolymer of maleic anhydride and vinyl dodecyl ether is employed as the dispersing agent.

EXAMPLE 3

Copolymer of vinylene carbonate, acrylamide and 1,4-butanediol divinyl ether

The following system was subjected to polymerization under the conditions described in Example 1 in the apparatus described in Example 1:

700 ml of liquid paraffin, 1.8 g of the copolymer of maleic anhydride and vinyl stearyl ether used in Example 2, 114.6 g of vinylene carbonate, 47.3 g of acrylamide, 16.2 g of 1,4-butanediol divinyl ether, 1.8 g of azodiisobutyronitrile and 100 ml of ethylene glycol.

The working up was likewise as described in Example 1.

The yield of crosslinked copolymer was 110 g (=62% of theory).

EXAMPLE 4

Copolymer of vinylene carbonate, N-vinylpyrrolidone and ethylene glycol dimethacrylate The following system was subjected to polymerization under the conditions of Example 1 in the apparatus according to Example 2:

800 ml of liquid paraffin, 0.18 g of copolymer of maleic anhydride and 1-octadecene according to Example 1, 103.2 g of vinylene carbonate, 44.4 g of N-vinylpyrrolidone, 29.5 g of ethylene glycol dimethacrylate, 1.8 g of azodiisobutyronitrile and 10 ml of polyethylene glycol (molecular weight 400).

The working up was as described in Example 1.

Yield: 120 g (67% of theory).

EXAMPLE 5

Copolymer of vinylene carbonate, vinyl acetate and 1,4-butanediol divinyl ether

The following system was subjected to polymerization under the conditions of Example 1 in the apparatus according to Example 2:

900 ml of isooctane, 1.25 g of copolymer of maleic anhydride and vinyl stearyl ether (as in Example 2), 43 g of vinylene carbonate, 43 g of vinyl acetate, 12 g of 1,4-butanediol divinyl ether, 1.3 g of azodiisobutyronitrile and 20 ml of polyethylene glycol (molecular weight 400).

Working up was as in Example 1, with the exception of the hexane wash which was omitted in this instance.

Yield: 52 g =53% of theory.

EXAMPLE 6

Copolymer of vinylene carbonate, vinyl acetate and 1,4-butanediol divinyl ether

The following system was subjected to polymerization under the conditions of Example 1 in the apparatus according to Example 2:

400 ml of hexane, 0.5 g of copolymer of maleic anhydride and vinyl stearyl ether (as in Example 2), 22 g of vinylene carbonate, 22 g of vinyl acetate, 6 g of 1,4-butanediol divinyl ether, 5 ml of diisopropyl percarbonate (40% in phthalate) and 20 ml of polyethylene glycol (molecular weight 400).

The polymerization time was 3 hours at 60° and one hour at 70°. The working up was as in Example 5.

Yield: 30 g (=60% of theory).

EXAMPLE 7

Copolymer of vinylene carbonate, vinyl acetate and 1,4-butanediol divinyl ether

The following system was subjected to polymerization under the conditions of Example 1 in the apparatus according to Example 2:

900 ml of liquid paraffin, 0.1 g of copolymer of maleic anhydride and vinyl stearyl ether (as in Example 2), 43 g of vinylene carbonate, 43 g of vinyl acetate, 20 g of 1,4-butanediol divinyl ether, 20 ml of dimethyl sulfoxide, 4 ml of polyethylene glycol (molecular weight 400) and 2 g of azodiisobutyronitrile.

The polymerization time was one hour at 80° and 3 hours at 90°.

The working up was as in Example 1.

Yield: 76 g (=71% of theory).

EXAMPLE 8

Copolymer of vinylene carbonate, N-vinylpyrrolidone and N,N-methylenebisacrylamide The following system was subjected to polymerization under the conditions of Example 1 in the apparatus according to Example 2:

900 ml of liquid paraffin, 1 g of copolymer of maleic anhydride and 1-octadecene (as in Example 4), 36.4 g of vinylene carbonate, 46.9 g of N-vinylpyrrolidone, 16.6 g of methylenebisacrylamide, 100 ml of dimethylformamide and 2 g of azodiisobutyronitrile.

The polymerization time was one hour at 80° and 3 hours at 90°.

Working up was by vigorous stirring with hexane for five hours to remove the liquid paraffin, vigorous stirring with methanol for five hours to remove the unreacted monomers and the dispersant, and vigorous stirring with acetone for two hours to remove the remaining constituents. The product was then dried in a vacuum oven at 50°–60° for 24 hours.

Yield: 65 g (=65% of theory).

EXAMPLE 9

Copolymer of vinylene carbonate, methyl methacrylate and 1,4-butanediol divinyl ether The following system was subjected to polymerization under the conditions of Example 1 in the apparatus according to Example 2:

900 ml of liquid paraffin, 0.2 g of copolymer of maleic anhydride and vinyl stearyl ether (according to Example 2), 43 g of vinylene carbonate, 50 g of methyl methacrylate, 20 g of 1,4-butanediol divinyl ether, 4 ml of polyethylene glycol (molecular weight 400) and 2 g of azodiisobutyronitrile.

The polymerization time was one hour at 80° and 3 hours at 90°.

Working up was as in Example 8.

Yield: 80 g (=70% of theory).

EXAMPLE 10

Copolymer of vinylene carbonate, N-vinylpyrrolidone and 1,4-butanediol divinyl ether The following system was subjected to polymerization under the conditions of Example 1 in the apparatus of Example 2:

800 ml of liquid paraffin, 1.5 g of copolymer of maleic anhydride and 1-octadecene (according to Example 1), 43 g of vinylene carbonate, 55.5 g of N-vinylpyrrolidone, 52 g of 1,4-butanediol divinyl ether, 100 ml of ethylene carbonate and 1.5 g of azodiisobutyronitrile.

The polymerization time was 2 hours at 80° and 2 hours at 90°.

The working up was as in Example 8.

Yield: 92 g (=61% of theory).

EXAMPLE 11

Copolymer of vinylene carbonate, vinylpyrrolidone and 1,4-butanediol divinyl ether.

The following system was subjected to polymerization under the conditions of Example 1 in the apparatus of Example 2:

900 ml of liquid paraffin, 0.2 g of copolymer of maleic anhydride and vinyl stearyl ether (according to Example 2), 43 g of vinylene carbonate, 55.5 g of N-vinylpyrrolidone, 20 g of 1,4-butanediol divinyl ether, 4 ml of polyethylene glycol (molecular weight 400), and 3 g of azodiisobutyronitrile (added in 2 portions).

The polymerization time was 30 hours at 70°. The first portion of 1.5 g of catalyst was added at the start of the polymerization time and the second portion of 1.5 g was added after 15 hours.

Working up was as in Example 8.

Yield: 91 g (=77% of theory).

EXAMPLE 12

Copolymer of vinylene carbonate, N-vinylpyrrolidone and N,N-methylenebisacrylamide The following system was subjected to polymerization under the conditions of Example 1 in the apparatus of Example 2:

900 ml of liquid paraffin, 0.2 g of copolymer of maleic anhydride and vinyl stearyl ether (according to Example 2), 37 g of vinylene carbonate, 48 g of N-vinylpyrrolidone, 15 g of N,N-methylenebisacrylamide, 106 ml of dimethylsulfoxide, 4 ml of polyethylene glycol (molecular weight 400) and 2 g of azodiisobutyronitrile.

The polymerization time was one hour at 80° and 4 hours at 90° C.

Working up was as in Example 8.

Yield: 79 g (79% of theory).

EXAMPLE 13

Copolymer of vinylene carbonate, N-vinylpyrrolidone and trisacryloylperhydrotriazine The following system was subjected to polymerization under the conditions of Example 1 in the apparatus of Example 2:

900 ml of liquid paraffin, 0.4 g of copolymer of maleic anhydride and vinyl stearyl ether (according to Example 2), 42 g of vinylene carbonate, 54.5 g of N-vinylpyrrolidone, 3.5 g of trisacryloylperhydrotriazine, 50 ml of diethylene glycol dimethyl ether and 2 g of azodiisobutyronitrile.

The polymerization time was 2 hours at 80° and 2 hours at 90°.

Working up was as in Example 8.

Yield: 69 g (=69% of theory).

EXAMPLE 14

Copolymer of vinylene carbonate, N-vinylpyrrolidone and N,N'-methylenebisacrylamide The following system was subjected to polymerization under the conditions of Example 1 in the apparatus of Example 2:

900 ml of liquid paraffin, 1 g of copolymer of maleic anhydride and 1-octadecene (according to Example 4), 23 g of vinylene carbonate, 60 g of N-vinylpyrrolidone, 17 g of N,N-methylbisacrylamide, 100 ml of dimethylformamide and 2 g of azodiisobutyronitrile.

The polymerization time was one hour at 80° and 3 hours at 90°.

Working up was as in Example 8.

Yield: 55 g (=55% of theory).

EXAMPLE 15

Copolymer of vinylene carbonate, N-vinylpyrrolidone and divinylethyleneurea

The following system was subjected to polymerization under the conditions of Example 1 in the apparatus of Example 2:

900 ml of liquid paraffin, 1 g of copolymer of maleic anhydride and 1-octadecene (according to Example 1), 26 g of vinylene carbonate, 34 g of N-vinylpyrrolidone, 40 g of divinylethyleneurea, 100 ml of dimethylformamide, 100 ml of glycerol and 2 g of azodiisobutyronitrile.

The polymerization time was one hour at 80° and 3 hours at 90°.

Working up was as described in Example 8.

Yield: 92 g (=92% of theory).

EXAMPLE 16

Copolymer of vinylene carbonate, N-vinylpyrrolidone and divinylethyleneurea

The following system was subjected to polymerization under the conditions of Example 1 in the apparatus of Example 2:

900 ml of liquid paraffin, 0.1 g of copolymer of maleic anhydride and vinyl stearyl ether (according to Example 2), 26 g of vinylene carbonate, 34 g of N-vinylpyrrolidone, 40 g of divinylethyleneurea, 30 ml of dimethylformamide, 70 ml of glycerol triacetate and 2 g of azodiisobutyronitrile.

The polymerization time was 3 hours at 80° and 1 hour at 90°.

Working up was by vigorous stirring with hexane for eight hours followed by vigorous stirring with acetone for one hour.

Yield: 78 g (=78% of theory).

Bulk density: 444 (g/l).

Bulk volume: 2.2 (ml/g).

Swelling: 3.8 (ml/g): (18 hours in tetrahydrofuran at 20° C.).

Pore volume: 0.52 (cm$^3$/g) (mercury porosimetry).

Mean pore diameter: 34 (nm).

The apparatus used to determine the swelling was that described in the Dechema Monograph volume 84 (1979) on pages 73 and 74. 100 mg of carrier were weighed into 5 ml of tetrahydrofuran.

EXAMPLE 17

Copolymer of vinylene carbonate, N-vinylpyrrolidone and divinylethyleneurea

The following system was subjected to polymerization under the conditions of Example 1 in the apparatus of Example 2:

900 ml of liquid paraffin, 0.1 g of copolymer of maleic anhydride and vinyl stearyl ether (according to Example 2), 30.5 g of vinylene carbonate, 39.5 g of N-vinylpyrrolidone, 30 g of divinylethyleneurea, 20 ml of dimethylformamide, 80 ml of glycerol triacetate and 2 g of azodiisobutyronitrile.

The polymerization time was 4 hours at 80° and 1 hour at 90°.

Working up was as described in Example 16.

Yield: 91 g (=91% of theory).

Bulk density: 497 (g/l).

Bulk volume: 2.0 (ml/g).

Swelling: 3.0 (ml/g):(18 hours in tetrahydrofuran at 20° C.)

Pore volume: 0.47 (cm$^3$/g) (mercury porosimetry).

Mean pore diameter: 30 (nm).

EXAMPLE 18

Copolymer of vinylene carbonate, N-vinylpyrrolidone and divinylethyleneurea

The following copolymerization was carried out in the apparatus described in Example 2:

First, 900 g of liquid paraffin (low viscosity) and 0.2 g of copolymer of maleic anhydride and vinyl stearyl ether according to Example 2 were initially introduced into the reaction flask. Then a mixture of 30.6 g of vinylene carbonate, 39.4 g of N-Vinylpyrrolidone, 30 g of divinylethyleneurea, 120 ml of dimethylformamide and 2 g of azodiisobutyronitrile was stirred until homogeneous in a beaker and then 60 ml of deionized water were added. This mixture was introduced into the reaction flask and, while stirring, the batch was heated to 70°, maintained at this temperature for 1 hour and then polymerization was completed at 80° for 4 hours. After cooling to about 50°, the copolymer was filtered off with suction, and then washed in the following sequence: heptane - methanol - acetone. After drying in vacuo, 80 g (80% of theory) of polymer were obtained.

EXAMPLE 19

Hydrolysis of the copolymer of vinylene carbonate, N-vinylpyrrolidone and N,N'-methylenebisacrylamide 30 g of the copolymer according to Example 14 above were stirred at reflux temperature in 150 ml of methanol and 50 ml of 2N sodium hydroxide solution in a 3-necked flask with a stirrer, reflux condenser and thermometer for about 4 hours. The carbonate group was converted into a glycol group with elimination of carbon dioxide. After neutralization with dilute hydrochloric acid, the copolymer was filtered off with suction and washed to neutrality with water/methanol. After drying in a vacuum oven at 60°, 22 g of the hydrolyzed copolymer were obtained.

Reaction with epichlorohydrin 20 g of the abovementioned product were treated with 150 ml of epichlorohydrin in the same apparatus, stirring for 5 hours at 113°–115°. After removing the unreacted epichlorohydrin by filtration under suction, the solid was washed several times with acetone and then dried in a vacuum oven at 50°. 25 g of a copolymer having a pale yellow color and containing oxirane were obtained. Analysis of the reaction product showed 364 μmol/g of epoxy units.

II. Reaction of the bead polymers with biologically active substances

EXAMPLE 20

12 ml of a trypsin solution (6.25 mg/ml, 345 U/ml), which was $1.6 \times 10^{-2}$ molar in benzamidine and 1 molar in potassium phosphate (buffer) and had a pH of 7.8, were added to 3 g of a carrier prepared according to Example 1. After binding overnight (16 h), the beads were thoroughly washed with 1 molar saline and with buffer solution. The yield of material moist from the filter funnel was 8.2 grams, with 270 units/g, measured in an autotitrator at 37° C. and pH 8.1 using N'-benzoyl-L-arginine ethyl ester hydrochloride (BAEE) as the substrate. This was 745 units/g based on dry weight. After balancing the initial activity and the activity in the wash water, the yield of binding (=the activity on the carrier:activity made available) which remained was 54%. The $\eta$ value was 0.56 ($\eta$=activity found/(activity made available minus activity in wash water)).

EXAMPLE 21

8 ml of a cephalosporinase solution, which contained 1,500 units/ml, 1 unit corresponding to the formation of 1 $\mu$mol of opened lactam ring per minute at a pH of 7.8 and 37° C., were added to 2 grams of a carrier prepared according to Example 1. The reaction was followed on an autotitrator by the consumption of sodium hydroxide solution.

After binding for one day, the carrier material was washed as in the previous example; about 7.5 grams of material which was moist from the filter funnel and was highly active, having at least 1,300 units/g or 5,000 units/g based on the dry weight, were obtained. The yield of binding was 81% after balancing ($\eta$=1).

EXAMPLE 22

0.4 ml of D-aminoacid oxidase solution containing 7 units/ml or 0.6 units/mg of protein, measured using cephalosporin C as substrate via the release of $H_2O_2$ according to German Offenlegungsschrift No. 2,219,454 at a pH of 8.1 and a temperature of 37° C. in 0.1 molar pyrophosphate buffer, were added to 0.1 g of carrier according to Example 15.

After 16 hours binding time, the enzyme bound to the carrier was washed and the activity was determined. Determination showed 1.25 units/g of material moist from the filter funnel and 5.4 units/g of dry material. The yield of binding was 19% ($\eta$=0.24).

EXAMPLE 23

22 mg of $\alpha$-amylase inhibitor (Tendamistat), which is 374,000 international inhibitor units=100%, dissolved in 5 ml of 1 molar sodium bicarbonate solution were added to 1 g of a carrier prepared according to Example 8. After 16 hours binding time, the carrier material with the bound enzyme was washed. The wash water contained 60% of the activity employed.

The carrier-bound inhibitor was able to bind $\alpha$-amylase.

EXAMPLE 24

1,200 $\mu$l of a penicillin acylase solution (40 mg/ml; 287 U/ml) in 1 molar potassium phosphate buffer of pH 8.0 were added to 0.2 g of the copolymer containing oxirane according to Example 19. After a binding time of 72 hours, the carrier was thoroughly washed with 1 molar saline and the abovementioned buffer solution. The yield of material moist from the filter funnel was 840 mg with 315 U/g, measured with an autotitrator at 37° and a pH of 7.8 using penicillin potassium as the substrate. 1,365 U/g, converted to dry weight, were obtained. After balancing the initial activity and the activity in the wash water, the yield of binding was 79% (activity over activity made available to the carrier). The value of $\eta$ was 0.81.

We claim:

1. A polymer essentially composed of units which are derived from vinylene carbonate or a derivative thereof which is substituted by a monovalent hydrocarbon radical having up to 8 carbon atoms, and of at least one other monomer which can be copolymerized with it, the mean particle size of the polymer particles being in the range from 20 to 800 um, wherein the polymer particles have an essentially spherical shape and a mean pore diameter of 5 to 1,000 nm.

2. The polymer as claimed in claim 1, wherein the mean pore diameter is 10 to 500 nm.

3. The polymer as claimed in claim 1, wherein the amount of vinylene carbonate units is 5 to 90 mole-% relative to the total polymer.

4. The polymer as claimed in claim 1, which, in addition to the vinylene carbonate units, contains units which are derived from monomers having hydrophilic groups.

5. The polymer as claimed in claim 4, which, as a consequence of incorporation of crosslinking monomer units, is crosslinked.

6. A process for the preparation of the polymer as claimed in claim 1, by polymerization of vinylene carbonate or a derivative thereof which is substituted by a monovalent hydrocarbon radical having up to 8 carbon atoms with at least one monomer which can be copolymerized with vinylene carbonate, in a liquid dispersing medium, which does not dissolve the monomers and the polymer under the polymerization conditions, in the presence of a radical initiator and a dispersion stabilizer, which comprises using, as the dispersion stabilizer, a copolymer of maleic anhydride and a vinyl alkyl ether having 6 to 30 carbon atoms in the alkyl group, or a vinyl ester having 6 to 30 carbon atoms in the carboxylic acid group, or a relatively long-chain $\alpha$-olefin having 8 to 30 carbon atoms.

7. The process as claimed in claim 6, wherein the dispersion stabilizer is used in amounts of 0.005 to 10% by weight relative to the mixture of monomers.

8. The process as claimed in claim 6, wherein the dispersion stabilizer is an alternating copolymer.

9. The process as claimed in claim 6, wherein the RSV value of the copolymer employed as a dispersion stabilizer is between 0.01 and 1.0 [dl/g] (measured in 0.6% strength solution in toluene at 25° C.).

10. The process as claimed in claim 6, wherein the vinyl alkyl ether is vinyl stearyl ether and the relatively long-chain $\alpha$-olefin is 1-octadecene.

11. The process as claimed in claim 6, wherein hydrocarbons having 6 to 20 carbon atoms, or low viscosity liquid paraffin is employed as the liquid dispersing agent.

12. The process as claimed in claim 6, wherein, in order to increase the porosity of the bead polymer, the polymerization system contains materials which are readily soluble in or miscible with the monomers and are virtually insoluble in the dispersing medium.

* * * * *